US011601782B2

(12) United States Patent
Chapman et al.

(10) Patent No.: US 11,601,782 B2
(45) Date of Patent: Mar. 7, 2023

(54) MULTIPLE DEVICE INTERSECTION USING GEO-TEMPORAL MOBILE APPLICATION DATA

(71) Applicant: Babel Street, Inc., Reston, VA (US)

(72) Inventors: Jeffrey Chapman, Landsowne, VA (US); Shon Myatt, Starkville, MS (US); James B. Haynie, New Orleans, LA (US)

(73) Assignee: Babel Street, Inc., Reston, VA (US)

( * ) Notice: Subject to any disclaimer, the term of this patent is extended or adjusted under 35 U.S.C. 154(b) by 19 days.

(21) Appl. No.: 17/240,930

(22) Filed: Apr. 26, 2021

(65) Prior Publication Data

US 2021/0337358 A1    Oct. 28, 2021

Related U.S. Application Data

(60) Provisional application No. 63/015,908, filed on Apr. 27, 2020.

(51) Int. Cl.
*H04W 24/00*  (2009.01)
*H04W 4/029*  (2018.01)
*G16Y 40/60*  (2020.01)

(52) U.S. Cl.
CPC ............. *H04W 4/029* (2018.02); *G16Y 40/60* (2020.01)

(58) Field of Classification Search
CPC ............................... H04W 4/029; G16Y 40/60
See application file for complete search history.

(56) References Cited

U.S. PATENT DOCUMENTS

| 10,511,938 | B1 * | 12/2019 | Marinovic | ............ | H04W 4/029 |
| 2011/0071881 | A1 | 3/2011 | Zheng et al. | | |
| 2011/0191284 | A1 | 8/2011 | Dalton et al. | | |
| 2017/0053538 | A1 | 2/2017 | Samarasekera et al. | | |
| 2017/0061625 | A1 | 3/2017 | Estrada et al. | | |
| 2017/0351657 | A1 | 12/2017 | Chapman et al. | | |
| 2021/0144510 | A1 * | 5/2021 | Yang | ...................... | G06Q 10/10 |

FOREIGN PATENT DOCUMENTS

EP         2247126 B1 *   1/2016   ............ H04W 4/029

OTHER PUBLICATIONS

International Search Report in International Patent Application No. PCT/US2021/029242, dated Jul. 28, 2021.

(Continued)

*Primary Examiner* — Erika A Washington
(74) *Attorney, Agent, or Firm* — Wiggin and Dana LLP

(57) ABSTRACT

A computer-implemented method for identifying device intersections using application data derived from multiple mobile devices. The method extracts the unique devices identified in a user defined area of interest (AOI) and generates individual geospatial layers for each device. The layers are derived from the metadata containing coordinates and associated timestamps for all available points of the device. Combining the individual layers will produce a convergence surface of polygonal intersections, indicating where devices have shared additional locations outside the initial AOI. Applying the timestamp to the resulting layer with a user defined time interval will generate a probability matrix of association.

8 Claims, 6 Drawing Sheets

(56) References Cited

OTHER PUBLICATIONS

Written Opinion of the International Searching Authority in International Patent Application No. PCT/US2021/029242, dated Jul. 28, 2021.
Lu et al., "Efficient Detection of Points of Interest from Georeferenced Visual Content", ACM, Nov. 10, 2017, retrieved on [Jun. 29, 2021]. Retrieved from the internet <URL: https://dl.acm.org/doi.pdf/10.1145/3150920> entire document.

* cited by examiner

MULTIPLE DEVICE INTERSECTION USING GEO-TEMPORAL MOBILE APPLICATION DATA

CROSS-REFERENCE TO RELATED APPLICATION

The present application claims the benefit of U.S. Provisional Patent Application No. 63/015,908, titled "Multiple Device Intersection Using Geo-Temporal Mobile Application Data" and filed Apr. 27, 2020, the contents of which are incorporated by reference herein in their entirety.

FIELD OF THE DISCLOSURE

The subject matter of the present disclosure generally relates to geo-temporal data, and more particularly relates to the generation of geo-temporal data from mobile devices as well as devices that produce diagnostic data such as those associated with the Internet of Things (IoT) that provide a capability to identify travel patterns and the rendezvous of those devices with others devices within space and time. These patterns and intersections can create probability matrices that indicate whether a pair of devices demonstrate travel or duration within an area that would denote an association.

BACKGROUND OF THE DISCLOSURE

Mobile applications and the applications commonly termed the Internet of Things (IoT) generate the vast amounts of geo-temporal data, data that possesses both geospatial coordinates and a time value within its metadata. Collecting this data by associating a device with a travel pattern allows opportunities to present products, services, intelligence, security, and predictive analysis to users based on user inputs such as locations visited or products consumed. Most of these methods compare single device patterns to known fixed locations. An example of such prior methods includes those described by U.S. Pat. No. 8,275,649, titled "Mining life pattern based on location history" and filed Sep. 18, 2009, the contents of which are incorporated by reference herein in their entirety.

A relatively simple method of serially searching a database of the traveling device locations against a static set of locations will satisfy the requirement to determine when two areas intercept as U.S. Pat. No. 8,275,649 outlines. Complexity arises when trying to determine when two or more dynamic devices converge throughout their individual and possibly independent travel patterns. Inferring relationships via proximity and time requires an exhaustive comparison of each datapoint within the search and, as more pairwise comparisons become required, the calculations exceed practical computing capability. Where a device may generate millions of points, the computation, using a balanced matrix between two devices for example, would generate over 500 billion comparisons using the following formula, known as the Condorcet Method, where N represents the number of datapoints present in a matrix per device application.

$$\frac{N(N-1)}{2} = \text{required pairwise comparisons}$$

Determining relationships based on the travel patterns and co-locations within both space and time is not a simple extension of being able to compare a moving object against a static point which is accomplished by N comparisons. Reducing the search space will in turn decrease the number of pairwise comparisons significantly and allow one to build a relationship matrix and identify devices across the temporal plain to determine where devices are converging outside an initial AoI simultaneously. This in effect will allow for the comparison of multiple devices to support force protection, investigations, direct marketing and business intelligence by understanding the movement of groups. Additionally, understanding the travel, proximity, and duration of multiple devices can assist in determining exposure to cross contamination and the spread of pathogens as with epidemiology without the need to draw on Personally Identifiable Information (PII).

The subject matter of the present disclosure is directed to overcoming, or at least reducing the effects of, one or more of the problems set forth above.

BRIEF SUMMARY OF THE DISCLOSURE

The disclosed method and system can provide the situational awareness as to intersections between mobile devices and/or other IoT devices that generate diagnostic geo-temporal data containing a location and timestamp for each datapoint produced. While methods exist that can determine movement of a single device, such as applications for marketing research, or multiple devices intersecting a known location, there are currently no methods that can determine relationships through the converging of dynamic devices from their initial origin to discover new areas of converging. The method includes identifying a set of devices within a specified area and creating an individual polygon from each device's point data for a user defined radius. The layering (mashing) of these polygons is used to generate intersections identifying a subset of points that share the same space.

The method computes the duration that each device remains within the identified intersection(s) by performing a temporal check. Comparing 1-dimensional overlap of time segments for each data point's timestamp and a time buffer defined by the user generates an aggregate of these segments to represent the total duration that a device is in an area. The device aggregate is then compared to all other device aggregates in that location to detect overlaps and the mutual duration of time within an intersection.

A relationship matrix with associated probabilities between devices can be computed using these duration markers and the number of rendezvous the devices make throughout their travel, indicating an association exists compared to random independent movement. The result is a system capable of identifying multiple devices with converging travel patterns. This information can support but is not limited to large-scale marketing research, security, research into group travel behavior, intelligence, advertising, social science, health science, and medical research such as epidemiology.

BRIEF DESCRIPTION OF THE DRAWINGS

The foregoing summary, preferred embodiments, and other aspects of the present disclosure will be best understood with reference to a detailed description of specific embodiments, which follows, when read in conjunction with the accompanying drawings, in which.

Like reference numbers and designations in the various drawings indicate like elements.

DETAILED DESCRIPTION

In the following detailed description, a reference is made to the accompanying drawings that form part hereof, and in which the specific embodiments that may be practiced is shown by way of illustration. These embodiments are described in sufficient detail to enable those skilled in the art to practice the embodiments and it is to be understood that the logical, mechanical, and other changes may be made without departing from the scope of the embodiments. The following detailed description is therefore not to be taken in a limiting sense.

Described now is a computer-implemented method for determining the relationships of dynamic mobile devices or IoT devices based on time and space (geo-temporal) data. The method uses polygon intersections of the devices geo-temporal history to generate an association matrix for each device originating from an Area of Interest (AoI). The Matrix is based on the number of times devices converge in both space and duration of time in other areas outside the initial AOI as defined by a user selected radius and time interval.

Figure 1:
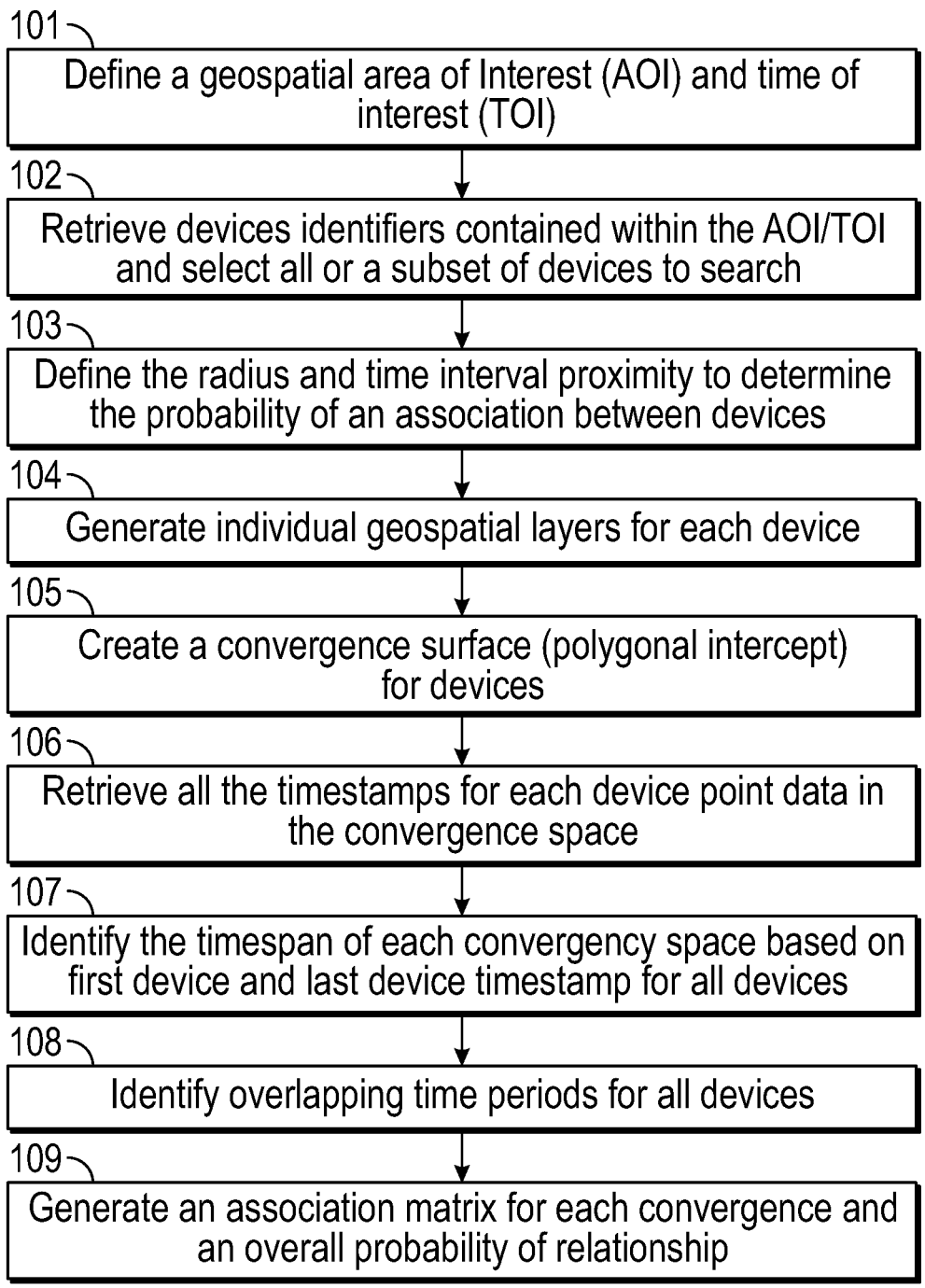
FIG. 1 is the sequential steps for identifying the relationships between devices producing geo-temporal data.
Figure 2:
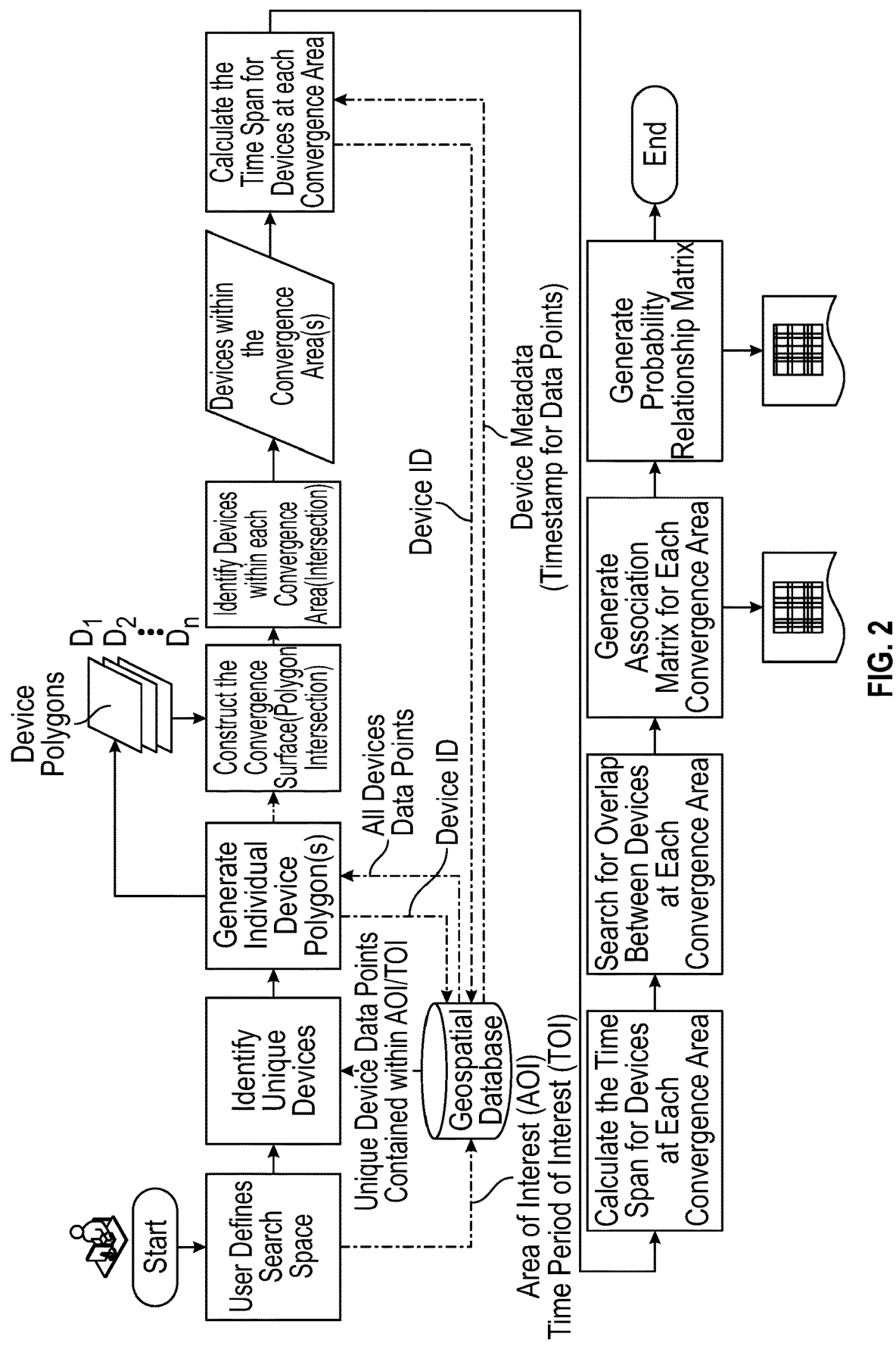
FIG. 2 is a concept flowchart of how the computer-implemented method would determine the intersecting polygons, time intervals, and relationship matrices.
Figure 3:
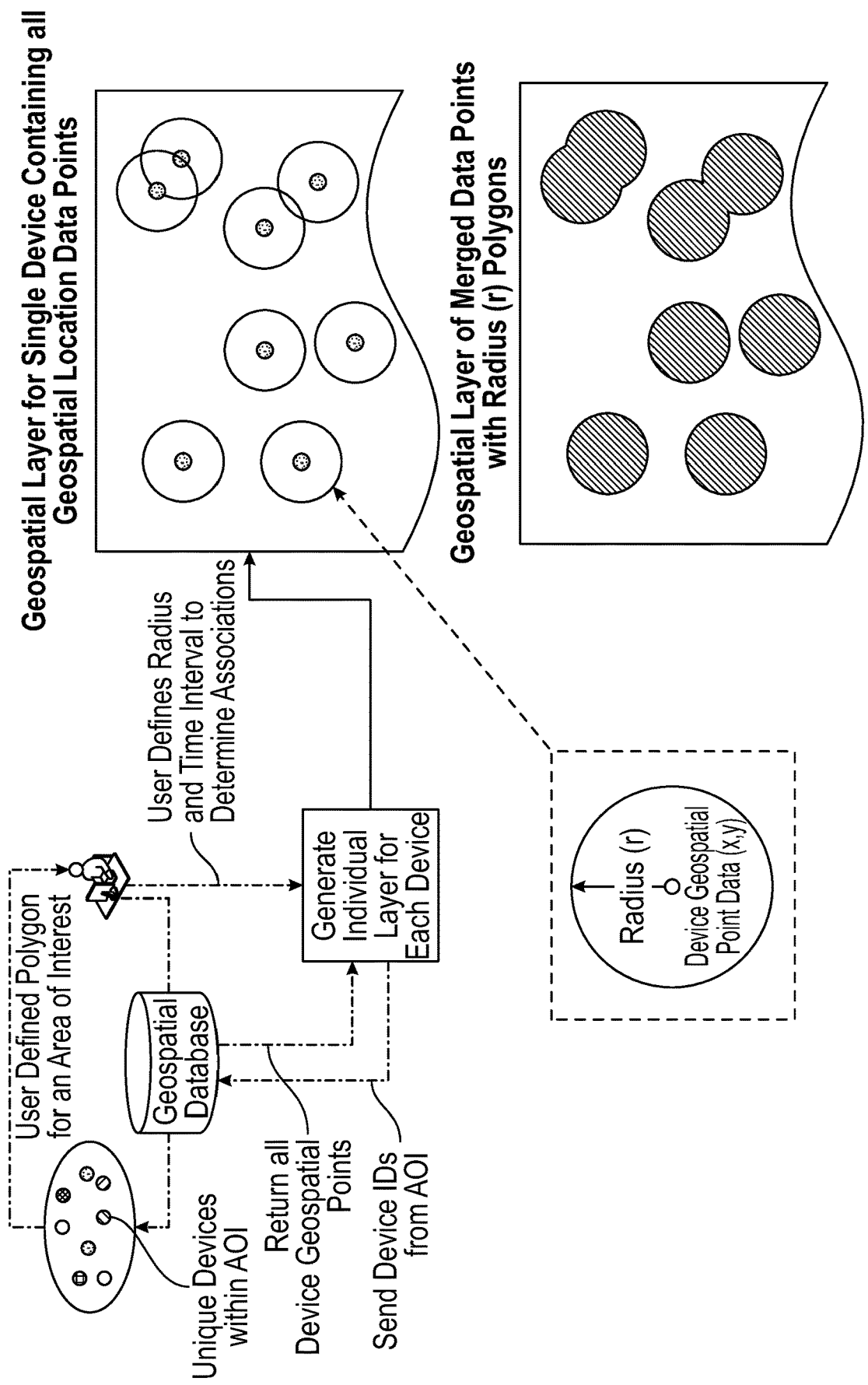
FIG. 3 depicts generating individual device polygons.

Referencing FIG. 1, the process initiates with a user creating a polygon around a geospatial area of interest (AoI) and defining a timespan of interest (ToI) (FIG. 1—step 101). Using the user polygon and timespan as the boundaries, access is made to a geospatial database containing all geo-temporal datapoints and the device identifiers that meet the criteria are returned (FIG. 1—step 102, FIG. 2, FIG. 3).

The user defines a radius for the data point (FIG. 1—step 103, FIG. 3) to create a polygon layer for each device within the AOI (or a selected subset of devices within the AOI). The system will retrieve all available datapoints for the individual device(s) selected and generate individual circular polygons for each datapoint (FIG. 3). The intersections of the circular polygons merge to produce a single polygon (FIG. 1—step 104, FIG. 3).

Figure 4:
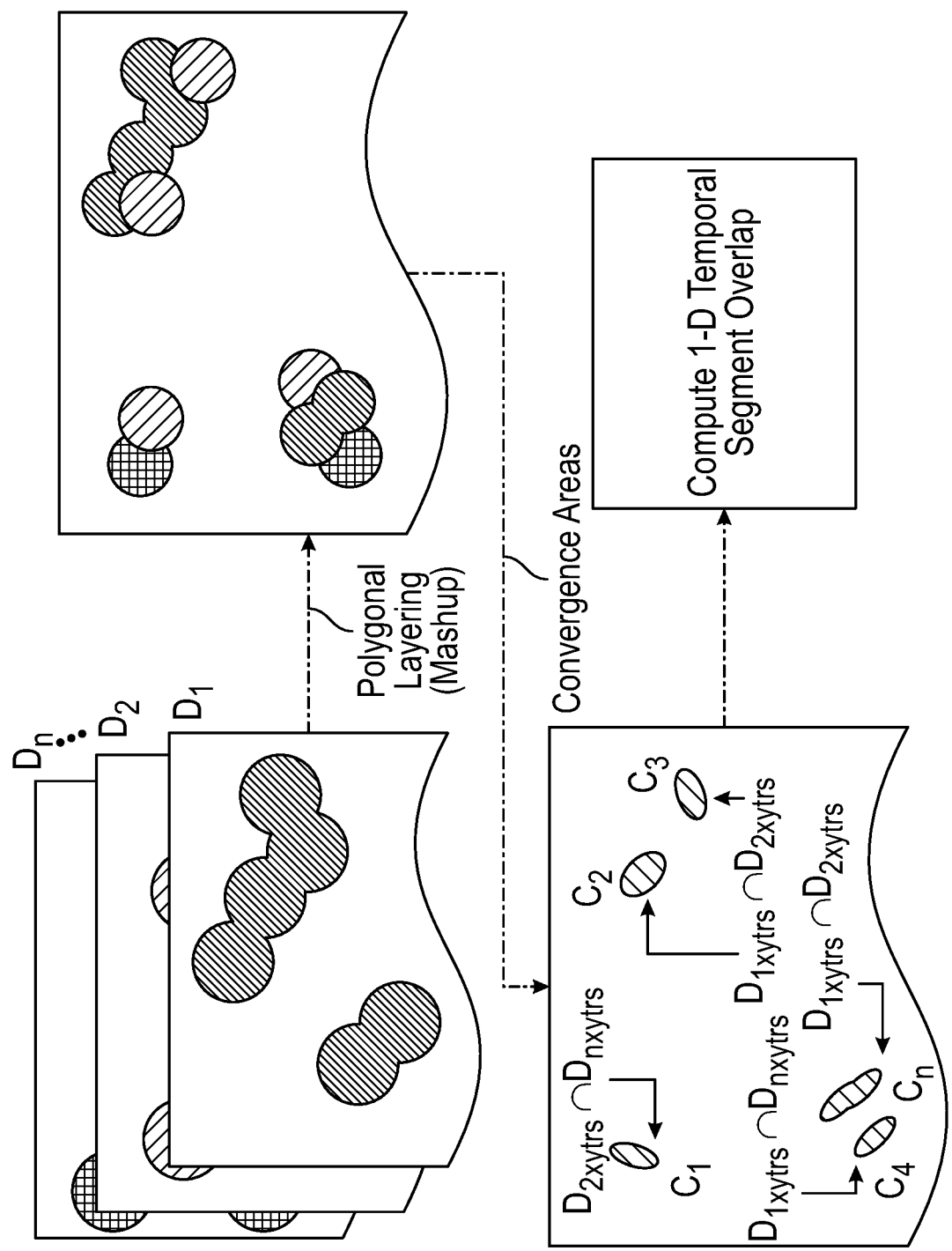
FIG. 4 depicts layering the device polygons into a single mashup to identify areas of interest.

The individual polygon layers representing a single device combine to form a surface (mashup) composed of intersections where the polygons layers overlap (FIG. 4). The intersection(s) indicates where devices share a common space outside the original AoI.

Figure 5:
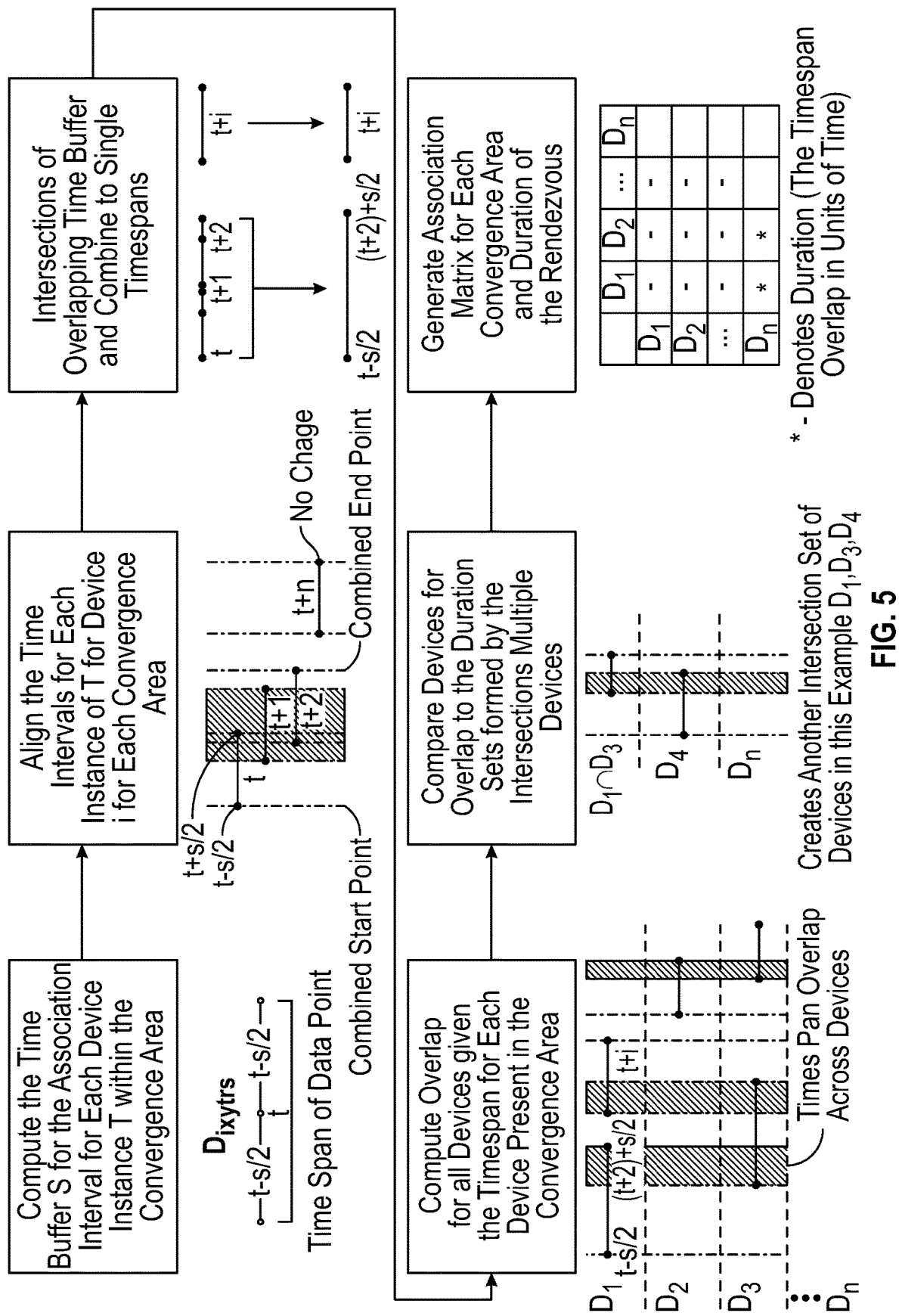
FIG. 5 depicts refining the solution space using the time interval variable and the metadata time stamp.

Since each datapoint contains a specific point in time, the user will define a timespan. The span will create a buffer to determine if other devices were present during this period by calculating one dimensional overlap. The initial step is to calculate the buffer, defined by the user, for each datapoint belonging to the same device (FIG. 1—step 106, FIG. 5). These time segments are then overlaid to determine the duration of the device within the intersection(s). The process repeats for all devices within the intersection(s) (FIG. 1—step 107, FIG. 5).

The time segments for all devices within an intersection (s) are overlaid to determine which devices are present within the intersection simultaneously and therefore represents a relationship (FIG. 1—step 108, FIG. 5).

Figure 6:
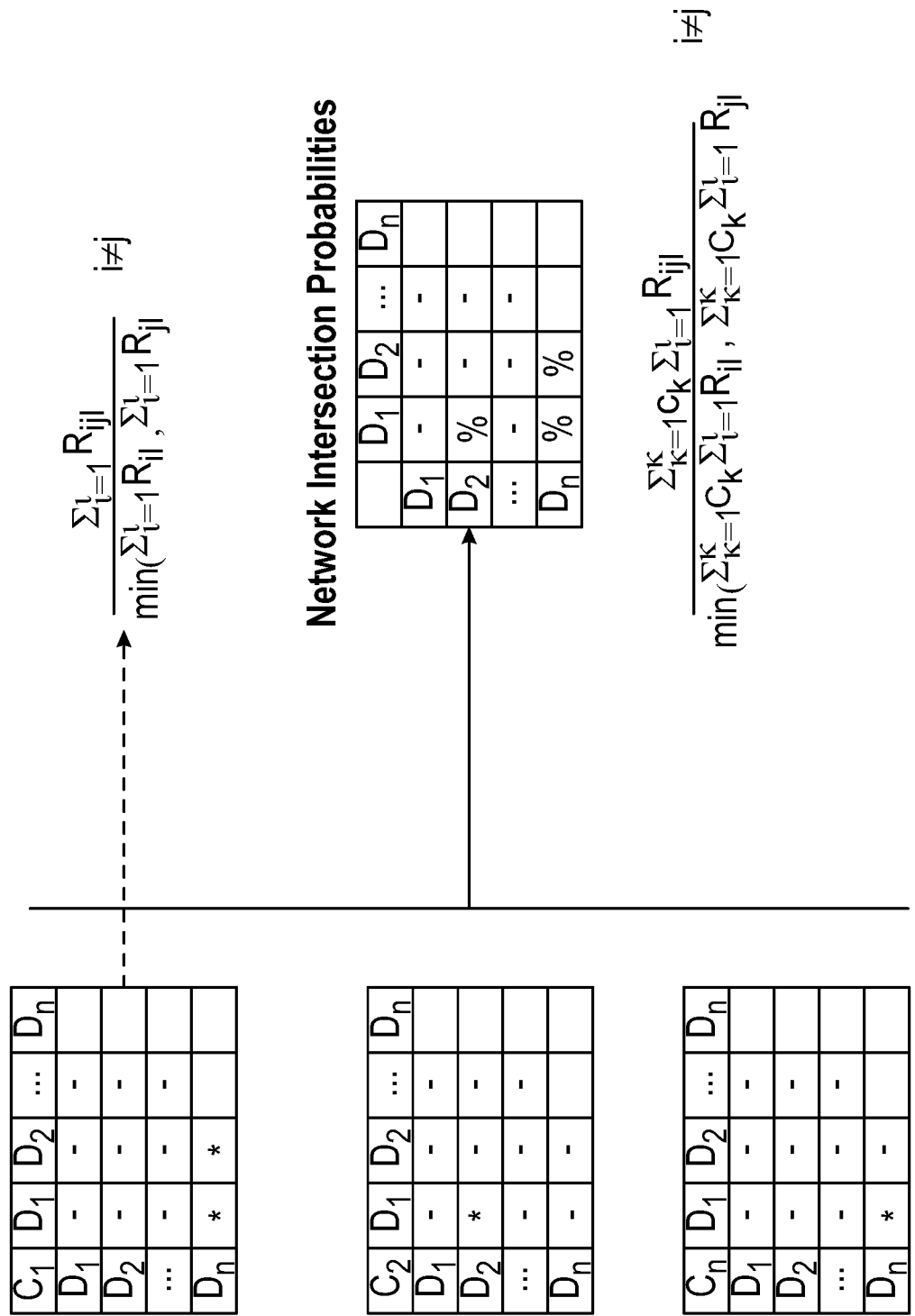
FIG. 6 depicts the generation of the relationship matrices for each polygon intersection and time interval and the overall relationship probability matrix.

An association matrix is populated based on the intersections that exist between pairs of devices. Probabilities can be computed using the duration when devices are co-located and the frequency of the rendezvous between multiple devices (FIG. 1—step 109, FIG. 6).

Algorithms and Heuristics

In an embodiment, several assumptions are made:
1. Given a buffer around the discrete timestamp for each device datapoint, overlapping intervals will determine the total duration at a location.
2. Relationships exist when devices repeatedly converge within a specified space and time interval.

In an embodiment method, the following variables can be used:

$D_{ixytrs}$
  where:
  D—Device
  i—Unique Device identifier, 1 . . . n
  x—$1^{st}$ coordinate of a two-coordinate system
  y—$2^{nd}$ coordinate of a two-coordinate system
  t—Unique timestamp for each for each i,x,y observation
  r—User defined Search Radius
  s—time overlap interval for determining associations $D_{ixyt}$
  where:
  D—Device
  i—Unique Device identifier, 1 . . . n
  x—$1^{st}$ coordinate of a two-coordinate system
  y—$2^{nd}$ coordinate of a two-coordinate system
  t—Unique timestamp for each i,x,y observation $C_k$
  Where:
  C—Convergence area
  k—1 . . . k $R_{il}$
  Where:
  R—Duration of device i
  i—1 . . . n
  l—Instance of device occurring in a unique convergence zone k, 1 . . . l $R_{ijl}$
  Where:
  R—Duration of device pairs i, j
  i—1 . . . n
  j—1 . . . m
  l—Instance of device pairs occurring in a unique convergence zone k, 1 . . . l Constructing a Polygon Layer for Each Unique Device In the construction of a geospatial surface to represent the entirety of a device's travel, the following algorithms for determining polygonal unions may be used. Additionally, a limit on the distance from the centroid can be used to prevent a single continuous polygon for devices that have generated high volumes of geo-temporal data.

Constructing the Intersections of Polygon Layers Determine the Convergence Space for Multiple Devices Construction of the intersections of separate devices and the intersecting search space can use a clipping algorithm such as the Vatti clipping Algorithm (Bala R. Vatti) which does not restrict the shape of the polygons and therefore allows for the complex shapes that may arise from the unions operations previously performed to represent a single device. The clipped portion (the intersection of the polygons) becomes the polygon representing the convergence area.

Determining the Duration of a Single Device for an Area where an Intersection of Polygons Exists.

Each datapoint contains a discrete timestamp and therefore there is a need to have a buffer to determine the duration of a device at a location. Creating a continuous interval based on the overlap of multiple samples creates an estimate of a device's total duration with an intersection. The duration can be calculated by comparing time intervals from the datapoints. The following heuristic will determine the duration.

For each $D_{ixytrs}$ contained within a set representing all the datapoints from a single device contained within the intersecting polygons, the time intervals can be compared based on the time overlap interval s.

For example $D_{ixytrs}$ the time internal is $$t - \frac{s}{2}, t + \frac{s}{2}$$

$D_{ixy(t+1)rs}$ represents the next datapoint denoted by the next timestamp of the same device contained within the intersecting polygons with the time interval represented by:

$$(t+1) - \frac{s}{2}, (t+1) + \frac{s}{2}$$

For all $D_i$ representing the same device, sorting is based on timestamp and the comparison of time duration intervals. If $$t + \frac{s}{2} \geq (t+1) - \frac{s}{2} \text{ and } t - \frac{s}{2} \leq (t+1) + \frac{s}{2}$$

exists then the overlap in time intervals is present and the new interval replaces both the time duration of both observations as $$t - \frac{s}{2}, (t+1) + \frac{s}{2}.$$

This process repeats until all timestamp comparisons for all observations of a single device are complete. This process is replicated for all devices present in the search. The result is a set of polygons that are separated by time intervals for each unique device.

Determining the Duration of Multiple Devices for an Area where an Intersection of Polygons (from Multiple Independent Devices) Exists.

Determining co-location of separate devices, the comparison is the same as determining the overlap for a single device where for each $D_{ixytrs}$ where i represents each unique device in the intersecting polygon (1, 2, 3, . . . n) therefore sorting the durations from earliest timestamp per convergence area the following comparison is made if $$(D_i)t + \frac{s}{2} \geq (D_j)t - \frac{s}{2} \text{ and } (D_i)t - \frac{s}{2} \leq (D_j)t + \frac{s}{2}$$

where i≠j then the two device share a geospatial area and time interval.

The duration of the two devices, $R_{ij}$, referenced in [0031] is calculated using:

$$\left(t - \frac{s}{2}\right) \text{ for } D_j - \left(t + \frac{s}{2}\right) \text{ for } D_i$$

The intersection of multiple devices is an extension of the process described in [0035] and [0037] for a pair of devices and follows same construct where the devices are sorted by earliest timestamps and the devices are compared with both the single device [0035] and to the duration interval between devices, therefore a timespan for a device set containing the devices that derived the interval.

The matrix for calculating the duration between devices for each convergence zone is the summation of the duration period for all instances of the pairs having overlapping time intervals.

$$\sum_{l=1}^{l} R_{ijl}$$

Each convergence zone can have a probability associated between pairs within a convergence zone. The intersection matrix is then computed using the summation of all the i,j pairs over all the convergence areas divided by the minimum duration total for each device within the network. The individual convergence zone C intersection matrix probability score for each device pair can be calculated as:

$$\frac{\sum_{l=1}^{l} R_{ijl}}{\min\left(\sum_{l=1}^{l} R_{il}, \sum_{l=1}^{l} R_{jl}\right)} \quad i \neq j$$

The overall network intersection matrix probability score calculation for each device pair:

$$\frac{\sum_{k=1}^{k} C_k \sum_{l=1}^{l} R_{ijl}}{\min\left(\sum_{k=1}^{k} C_k \sum_{l=1}^{l} R_{il}, \sum_{k=1}^{k} C_k \sum_{l=1}^{l} R_{jl}\right)} \quad i \neq j$$

The result is a series of probability scores which may identify transitive intersections, such as a high probability between pairs A and B, B and C and therefore there is a network or an association between A and C in continuum until the associations are complete.

A count of unique intersections between devices with regards to time can provide another method to determine a systematic intersection or a repeating pattern of device movement. The calculation is the maximum index for l, the instance of device pairs occurring in a unique convergence zone 1 . . . l for unique convergence zone k divided by the maximum index for the individual device with the fewest instances at convergence zone K will generate a metric for determining randomness of devices converging both geospatially and temporally.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed:

1. A method of evaluating associations between electronic devices, comprising the steps of:
    defining a geospatial area of interest (AOI) and a time of interest (TOI);
    identifying devices contained within the AOI and TOI;
    selecting at least a subset of the identified devices;
    defining a radius and a time interval proximity;
    generating at least one individual geospatial layer for each selected device;
    creating a convergence surface for the selected devices;
    retrieving a set of timestamps for each selected device in the convergence surface;
    identifying a timespan for each of the selected devices in the convergence surface based on a first device timestamp and a last device timestamp;
    identifying one or more overlapping timespans for the selected devices; and
    generating an association matrix including the one or more overlapping timespans.

2. The method of claim 1 further comprising the step of generating an overall probability of association matrix.

3. The method of claim 1 wherein the convergence surface is defined by polygonal intersections of the geospatial layers.

4. The method of claim 1 further comprising the step of calculating an individual convergence zone C intersection matrix probability score according to:

$$\frac{\sum_{l=1}^{l} R_{ijl}}{\min\left(\sum_{l=1}^{l} R_{il}, \sum_{l=1}^{l} R_{jl}\right)}, i \neq j.$$

5. The method of claim 1 further comprising the step of calculating an overall network intersection matrix probability score for each device pair according to:

$$\frac{\sum_{k=1}^{k} C_k \sum_{l=1}^{l} R_{ijl}}{\min\left(\sum_{k=1}^{k} C_k \sum_{l=1}^{l} R_{il}, \sum_{k=1}^{k} C_k \sum_{l=1}^{l} R_{jl}\right)}, i \neq j.$$

6. A computer-implemented method for identifying device intersections using application data derived from a plurality of mobile devices, comprising the steps of:
    identifying a plurality of mobile devices contained in an initial user defined area of interest (AOI) and generating a set of individual geospatial layers for each of the devices, wherein the set of individual geospatial layers are derived from a set of metadata containing a plurality of coordinate points and a plurality of associated timestamp points for each of the devices;
    combining the individual layers to produce a convergence surface of polygonal intersections indicating where devices have shared one or more additional locations outside the initial user defined AOI; and
    applying the timestamps to the resulting convergence surface with a user defined time interval to generate a probability matrix of association for the one or more additional locations.

7. The method of claim 6 further comprising the step of calculating an individual convergence zone C intersection matrix probability score for the one or more additional locations according to:

$$\frac{\sum_{l=1}^{l} R_{ijl}}{\min\left(\sum_{l=1}^{l} R_{il}, \sum_{l=1}^{l} R_{jl}\right)}, i \neq j.$$

8. The method of claim 6 further comprising the step of calculating an overall network intersection matrix probability score for each device pair having associations in the one or more additional locations according to:

$$\frac{\sum_{k=1}^{k} C_k \sum_{l=1}^{l} R_{ijl}}{\min\left(\sum_{k=1}^{k} C_k \sum_{l=1}^{l} R_{il}, \sum_{k=1}^{k} C_k \sum_{l=1}^{l} R_{jl}\right)}, i \neq j.$$

* * * * *